(12) United States Patent
Takezawa et al.

(10) Patent No.: US 6,749,774 B2
(45) Date of Patent: Jun. 15, 2004

(54) CONDUCTIVE ADHESIVE AND CONNECTION STRUCTURE USING THE SAME

(75) Inventors: Hiroaki Takezawa, Nara (JP); Takashi Kitae, Osaka (JP); Yukihiro Ishimaru, Osaka (JP); Tsutomu Mitani, Hyogo (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/309,596

(22) Filed: Dec. 3, 2002

(65) Prior Publication Data

US 2003/0127632 A1 Jul. 10, 2003

Related U.S. Application Data

(62) Division of application No. 09/751,621, filed on Dec. 29, 2000, now Pat. No. 6,521,144.

(30) Foreign Application Priority Data

Jan. 7, 2000 (JP) ......................................... 2000-001526

(51) Int. Cl.⁷ .................................................. H01B 1/22
(52) U.S. Cl. ........................................ 252/512; 252/514
(58) Field of Search ................................ 252/512, 514; 156/47

(56) References Cited

U.S. PATENT DOCUMENTS

| 4,122,143 A | 10/1978 | Momotari et al. |
| 5,736,070 A | 4/1998 | Murakami et al. |
| 5,925,973 A | 7/1999 | Eda et al. |

FOREIGN PATENT DOCUMENTS

| JP | 5-159622 | 6/1993 |
| JP | 9-176285 | 7/1997 |

OTHER PUBLICATIONS

"Development of Functional Adhesives and the New Technology"; Miyairi, Hiroo; CMC, Jun. 30, 1997; with partial English translation.

Primary Examiner—Mark Kopec
(74) Attorney, Agent, or Firm—Merchant & Gould P.C.

(57) ABSTRACT

A mounting technique with improved adhesive strength and higher reliability against bending stress is provided with the use of a conductive adhesive including a binder resin and a metal filler as main components, in which a functional group is introduced into the molecular chain of the binder resin to form a multidentate bonding with an electrode metal easily. As a thermoplastic resin, at least two kinds of functional groups selected from the group consisting of a carbonyl group, a carboxyl group, an amino group, an imino group, an iminoacetic acid group, an iminopropionic acid group, a hydroxyl group, a thiol group, a pyridinium group, an imido group, an azo group, a nitrilo group, an ammonium group and an imidazole group are introduced. Accordingly, a strong bond with the electrode metal can be achieved. The conductive adhesive is screen-printed to an electrode disposed on a substrate, and after an electrode of a component is mounted, the structure is heated so as to create a mounted structure.

7 Claims, 1 Drawing Sheet

CONDUCTIVE ADHESIVE AND CONNECTION STRUCTURE USING THE SAME

This application is a divisional of Ser. No. 09/751,621 Dec. 29, 2000, now U.S. Pat. No. 6,521,144.

FIELD OF THE INVENTION

The present invention relates to a conductive adhesive used for solder-free mounting of electronic components and a structure connected by using the same.

BACKGROUND OF THE INVENTION

In recent years, due to the increased environmental consciousness, the electrical industry now faces the movement to abolish totally lead-containing solder used for mounting of electronic components, and this movement is becoming significant.

As for lead-free mounting techniques, mounting techniques using lead-free solder have been developed keenly and a part of the development has come into practical use. However, still a number of problems remains to be solved, such as influence of a high mounting temperature on low heat-resistant components or lead-free electrodes.

On the other hand, only a few examples of lead-free mounting with the use of a conductive adhesive has been reported so far, which has the following advantages besides the aspect of lead-free mounting.

First, the processing temperature of around 150° C. is lower than the temperature for soldering, and electronic components with higher performance can be realized with low cost. Secondly, the specific gravity of a conductive adhesive is about half that of solder, so that electronic equipment can be lightened more easily. Thirdly, since the connection is not achieved by means of metal as in soldering, metal fatigue does not occur, and the reliability of mounting is excellent.

Therefore, it is expected that a revolutionary mounting process that fulfills the needs of environment, low cost, and high reliability can be realized by completing the mounting technique using a conductive adhesive.

The problem with the use of a conductive adhesive for mounting is that the adhesive strength is lower than that of solder. In particular, the strength against bending stress is about 1/10 of that of solder, so that an electronic component with a large area to which bending stress easily is applied sometimes suffers from the separation of the electrode with the conductive adhesive at the interface, thereby causing connection failures.

Numerous attempts to improve the adhesive strength have been reported, but not even one technique is capable of achieving the same strength as that of solder. One representative example will be shown below.

As described in the publication supervised by Hiroo Miyairi, "Development of Functional Adhesives and the New Technology" (edited by CMC, Jun. 30, 1997, 194 pages), for example, a number of techniques to improve the adhesive strength by adding an organic metal called a silane coupling agent into the adhesive material, which can form a chemical bond with both resin and metal, has been reported.

However, the aforementioned techniques utilize either a dehydration reaction or a substitution reaction, so that the reactivity of the coupling agent with resin or with metal was poor, and the conditions (temperature, concentration of hydrogen ion, etc.) for optimizing the reaction could not be determined clearly, and so forth. Therefore, a considerable improvement of the adhesive strength was difficult to be achieved.

Furthermore, JP9(1997)-176285A proposes the use of a resin with a phosphoric ester group introduced into the skeleton as a binder resin. According to this method, the functional group in the binder resin is adsorbed to the metal, so that some improvement of the adhesive strength can be achieved. However, the adsorptive power is poor in comparison with a covalent bond or a coordinate bond, so that considerably improved effects could not be obtained.

As described above, the improvement of the adhesive strength has been the key factor to make the practical use of the mounting technique using a conductive adhesive.

SUMMARY OF THE INVENTION

It is an object of the present invention to solve the conventional problems described above by providing a conductive adhesive having considerably improved adhesive strength and higher reliability against bending stress. Another object of the present invention is to provide a structure connected by using this conductive adhesive.

To achieve the above object, a conductive adhesive of the present invention includes a binder resin and a metal filler as main components, wherein the binder resin contains a functional group in its molecular chain that forms a multidentate bonding with an electrode metal after the binder resin is adhered.

A connection structure of the present invention is formed by using a conductive adhesive to connect the adhesive with an electrode electrically, wherein the conductive adhesive includes a binder resin and a metal filler as main components, and the binder resin contains a functional group in its molecular chain that forms a multidentate bonding with an electrode metal after the binder resin is adhered.

In the present invention, the multidentate bonding refers to a state in which multidentate ligands (a plurality of chelating ligands) introduced into the binder resin form coordinate bonds with the electrode metal. In other words, the adhesion is not achieved only by using the ordinary weak van der Waal's power by hydrogen bonding, but instead, a chemical bond (coordinate bond) is formed between the binder resin and the electrode.

The method of introducing a multidentate ligand into a binder resin will be explained by way of the following embodiments.

Embodiment 1

In the first method, a resin into which a desired multidentate ligand was introduced was used as an additive component in the binder resin (a reactive thinner, a hardener, or the like).

For example, a linear epoxy resin with a molecular chain into which a dicarbonyl group expressed by the chemical formula 1 below was introduced is mixed with a ring-opening catalyst, which then is applied to the surface of an electrode (Cu foil). When the resin is heated and hardened, the dicarbonyl group in the central part of the molecule forms a coordinate bond with the electrode (Cu foil) expressed by the chemical formula 2 below. Naturally, the epoxy rings at the both ends of the molecule open and form bridge bonds.

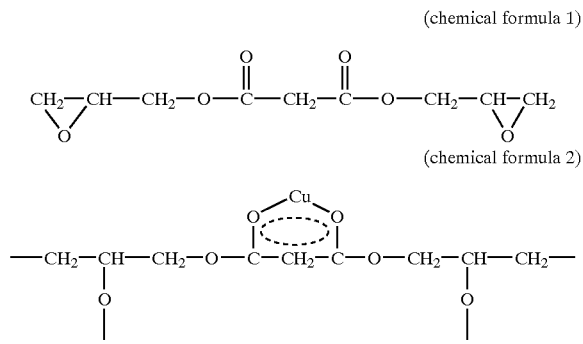

(chemical formula 1)

(chemical formula 2)

The binder resin used here includes as the main component an ordinary epoxy resin without any ligand (bisphenol A, bisphenol F, a novolak epoxy resin). The above resin into which the multidentate ligand was introduced is used by mixing and kneading so as to be contained in the binder resin in an amount between 10 and 50 wt %.

Furthermore, a ligand can be introduced into a resin to be used as a hardener in the binder resin, not only for the reactive thinner.

Embodiment 2

In the second method, a resin into which a desired multidentate ligand was introduced was used as the main component (the component contained in the largest amount) in the binder resin.

For example, a bisphenol F-type epoxy resin with a molecular chain into which a dicarbonyl group expressed by the chemical formula 3 below was introduced is mixed with a ring-opening catalyst, which then is applied to the surface of an electrode (Cu foil). When the resin is heated and hardened, the dicarbonyl group in the central part of the molecule forms a coordinate bond with the electrode (Cu foil) as in Embodiment 1.

contained in an amount between 75 and 95 wt %. Besides, if necessary, a hardener, a hardening catalyst, a crosslinking agent, and a ring-opening catalyst for the binder resin, a dispersing agent for the metal filler, a viscosity modifier, a pH modifier, or the like may be added optionally. Therefore, in the present invention, "main components" in the "including a binder resin and a metal filler as main components" refers to the constitution in which the binder resin and the metal filler together comprise at least 90 wt % of the conductive adhesive.

Furthermore, in the adhesive and the connection structure described above, it is preferable that at least two functional groups are present, which may be the same or different, selected from the group consisting of a carbonyl group, a carboxyl group, an amino group, an imino group, an iminoacetic acid group, an iminopropionic acid group, a hydroxyl group, a thiol group, a pyridinium group, an imido group, an azo group, a nitrilo group, an ammonium group and an imidazole group.

Furthermore, in the adhesive and the connection structure described above, it is preferable that the metal filler is at least one particle selected from the group consisting of silver, silver-plated nickel and silver-plated copper. When the surface of the metal filler is silver, it does not react with the ligand of the binder resin but the ligand reacts selectively with the electrode metal. However, when the ligand of the binder resin is contained in a large amount, even if copper is used as the metal filler, for example, since not all the ligands react with the metal filler, copper also can be used as the metal filler.

Furthermore, in the adhesive and the connection structure described above, it is preferable that the binder resin is at least one resin selected from a thermoplastic resin and a thermosetting resin.

Furthermore, in the adhesive and the connection structure described above, it is preferable that the thermoplastic resin is at least one resin selected from the group consisting of a polyester resin, a silicone resin, a vinyl resin, a vinyl chloride resin, an acrylic resin, a polystyrene resin, an ionomer resin, a polymethylpentene resin, a polyimide resin, a polycarbonate resin, a fluororesin and a thermoplastic epoxy resin.

(chemical formula 3)

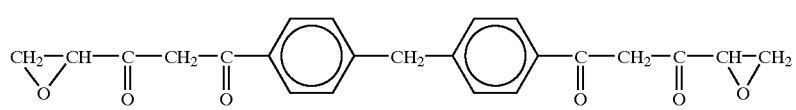

The binder resin used here includes as the accessory component an ordinary epoxy resin without any ligand (a reactive thinner, a hardener, or the like). The above resin into which the multidentate ligand was introduced is used by mixing and kneading so as to be contained in the binder resin in an amount between 30 and 100 wt %.

In the adhesive and the connection structure of the present invention described above, it is preferable that the multidentate bonding is formed in a number between 2 and 4. Naturally, the number of the multidentate bonding may be larger.

Furthermore, in the adhesive and the connection structure described above, it is preferable that the resin containing a functional group in its molecular chain that forms a multidentate bonding is present in an amount between 10 and 100 wt % of the total resin.

Furthermore, in the adhesive and the connection structure described above, it is preferable that, taking the conductive adhesive as 100 wt %, the binder resin is contained in an amount between 6 and 25 wt %, and the metal filler is According to the invention described above, the mounting technique by the conductive adhesive with considerably improved adhesive strength can be realized.

When the conductive adhesive of the present invention and the electrode metal contact each other, the ligand of the binder resin very easily reacts with the metal, so that the ligand is coordinated quickly with the electrode metal to form a chelating ligand, i.e. a strong chemical bonding. Since the ligand is bonded to the molecular chain of the resin, the bonding also is strengthened between the binder resin and the electrode metal as well as between the conductive adhesive and the electrode metal.

The connection structure of the present invention is formed by electrically connecting the conductive adhesive of the present invention with the electrode, so that this connection structure has improved adhesive strength than conventional connection structures. Moreover, since the thermoplastic resin has excellent flexibility in comparison with a thermosetting resin, this conductive adhesive can achieve a bonding with excellent stress relaxation capability against bending stress.

The connection structure of the present invention preferably is formed by mounting a component and a substrate by using the conductive adhesive described above, which can improve the adhesive strength against bending stress even more.

The present invention can be used in place of the conventional solder, for example, as a conductive adhesive to bond a semiconductor substrate with an electronic component chip. Furthermore, the conductive adhesive also can be applied to a conductive paste by filling the conductive adhesive into through holes made in an electrical insulating base material so as to achieve electrical continuity in the thickness direction of the electrical insulating base material.

DETAILED DESCRIPTION OF THE INVENTION

Figure 1:
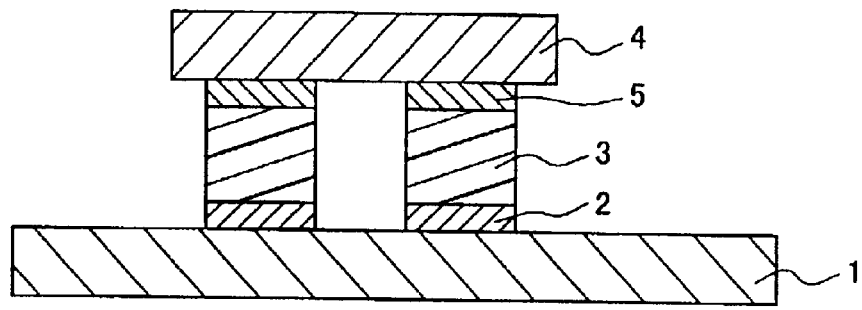
FIG. 1 is a cross-sectional view showing a mounted structure used for the evaluation of one embodiment of the present invention.

Hereinafter, the present invention will be described by way of examples with reference to drawings.
Common Experimental Method FIG. 1 is a side view of a mounted structure used for the evaluation. A conductive adhesive 3 is screen-printed onto an electrode 2 disposed on a substrate 1, and after an electrode 5 of a component 4 is mounted, the structure is heated in an oven at 150° C. for 30 minutes. Thus, the mounted structure was created. The material used for the substrate 1 and the component 4 was the same, and the material used for the electrode 2 and the electrode 5 was the same.

Figure 2:
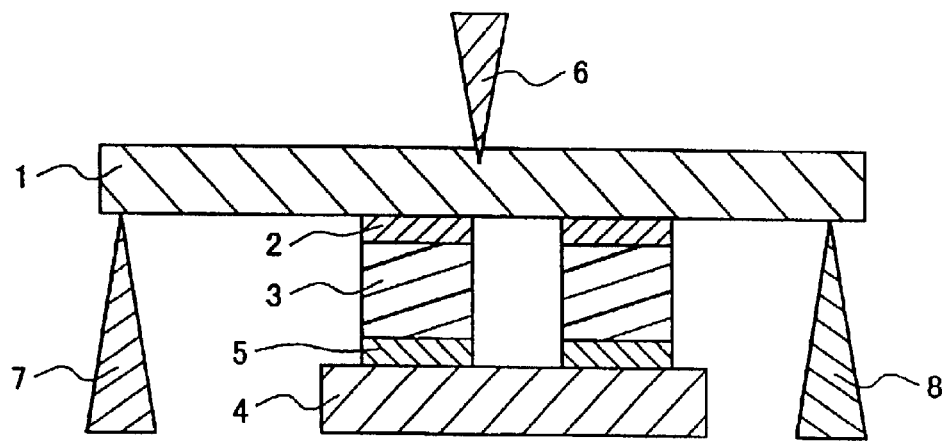
FIG. 2 is a cross-sectional illustrative view showing the evaluation method of one embodiment of the present invention.

The evaluation method is shown in FIG. 2. First, pressure was provided to the component 4 from the rear side of the mounted structure created as above by using a substrate pushing jig 6. The amount of deflection was measured when the connection resistance had risen to at least twice as much as the initial value. Then, the adhesive strength against the bending stress was evaluated. The distance between substrate fixing jigs 7 and 8 was determined to be 100 mm.

The substrate and the component will be described more in detail.

(1) Component: 0 ohmic resistance base material; alumina or a glass epoxy substrate (3216 size) electrode specification; as shown in Table 1
(2) Substrate base material; alumina or a glass epoxy substrate (30×150×1.6 mm) electrode specification; as shown in Table 1
(3) Conductive adhesive filler; silver powder (85 wt %) (average particle diameter: 3 to 10 μm) binder resin (15 wt %); as shown in Table 1

Hereinafter, the respective embodiments will be explained in detail. In Examples 1 and 2, the conductive adhesive includes a material in which a functional group was introduced into a thermosetting resin. In Examples 3 and 4, the conductive adhesive includes a material in which a functional group was introduced into a thermoplastic resin.

EXAMPLE 1

Example 1 is an example, as already explained in Embodiment 1, in which a resin into which a multidentate ligand was introduced was used as an additive component (a reactive thinner).

The binder resin used for the conductive adhesive was obtained by mixing 15 wt % of a reactive thinner in which a dicarbonyl group expressed by the chemical formula 4 below was introduced into its molecular chain, 75 wt % of a bisphenol F epoxy resin, 5 wt % of a hardener (maleic anhydride), and 5 wt % of a solvent (butyl carbitol acetate).

(chemical formula 4)

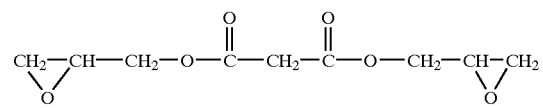

As a result, in comparison with the cases of Comparative Example 1 (a conventional conductive adhesive), Comparative Example 5 (a silane coupling agent was added), and Comparative Example 7 (an epoxy resin into which a phosphoric ester group was introduced), the amount of deflection at the time of NG rose, and the adhesive strength against the bending stress improved.

EXAMPLE 2

The binder resin used for the conductive adhesive was the same epoxy resin as in Example 1 in which a dicarbonyl group was bonded to its side chain (chemical formula 4 above). A conventional Cu thick foil was used as the electrode.

As a result, in comparison with the cases of Comparative Example 2 (a conventional conductive adhesive), Comparative Example 6 (a silane coupling agent was added), and Comparative Example 8 (an epoxy resin into which a phosphoric ester group was introduced), the amount of deflection at the time of NG rose, and the adhesive strength against the bending stress improved.

EXAMPLE 3

Except that a thermoplastic silicone resin was used in which a dicarbonyl group was introduced into the side chain of silicone expressed by the chemical formula 5 below, the constitutions were the same as in Example 1.

(chemical formula 5)

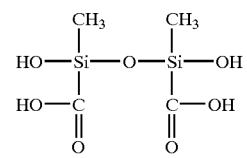

As a result, in comparison with the cases of Comparative Example 1 (a conventional conductive adhesive), Comparative Example 5 (a silane coupling agent was added), and Comparative Example 7 (an epoxy resin into which a phosphoric ester group was introduced), the amount of deflection at the time of NG rose, and the adhesive strength against the bending stress improved.

EXAMPLE 4

The binder resin used for the conductive adhesive was the resin in which a dicarbonyl group was bonded to the side chain of a silicone resin expressed by the chemical formula 4 above. A conventional Cu foil was used as the electrode.

As a result, in comparison with the cases of Comparative Example 2 (a conventional conductive adhesive), Comparative Example 6 (a silane coupling agent was added), and Comparative Example 8 (an epoxy resin into which a phosphoric ester group was introduced), the amount of deflection at the time of NG rose, and the adhesive strength against the bending stress improved. Furthermore, the adhesive strength was higher than in Example 2.

EXAMPLE 5

Except that an epoxy resin was used in which the ligand to be introduced into the resin was changed to an aminocarbonyl group in Example 1 expressed by the chemical formula 6 below, the constitutions were the same as in Example 1.

(chemical formula 6)

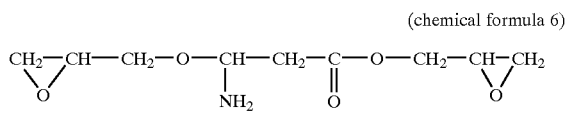

As a result, in comparison with the cases of Comparative Example 1 (a conventional conductive adhesive), Comparative Example 5 (a silane coupling agent was added), and Comparative Example 7 (an epoxy resin into which a phosphoric ester group was introduced), the amount of deflection at the time of NG rose, and the adhesive strength against the bending stress improved.

EXAMPLE 6

Except that the electrode was changed to a calcined Cu thick foil, the constitutions were the same as in Example 5.

As a result, in comparison with the cases of Comparative Example 2 (a conventional conductive adhesive), Comparative Example 6 (a silane coupling agent was added), and Comparative Example 8 (an epoxy resin into which a phosphoric ester group was introduced), the amount of deflection at the time of NG rose, and the adhesive strength against the bending stress improved.

EXAMPLE 7

Except that an epoxy resin was used in which the ligand to be introduced into the resin was changed to a dicarbonyl group in Example 1 expressed by the chemical formula 7 below, the constitutions were the same as in Example 1.

(chemical formula 7)

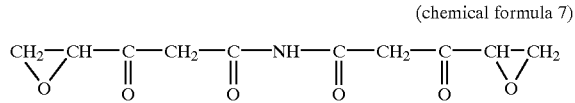

As a result, in comparison with the cases of Comparative Example 1 (a conventional conductive adhesive), Comparative Example 5 (a silane coupling agent was added), and Comparative Example 7 (an epoxy resin into which a phosphoric ester group was introduced), the amount of deflection at the time of NG rose, and the adhesive strength against the bending stress improved.

EXAMPLE 8

Except that the electrode was changed to a calcined Cu thick foil, the constitutions were the same as in Example 7.

As a result, in comparison with the cases of Comparative Example 2 (a conventional conductive adhesive), Comparative Example 6 (a silane coupling agent was added), and Comparative Example 8 (an epoxy resin into which a phosphoric ester group was introduced), the amount of deflection at the time of NG rose, and the adhesive strength against the bending stress improved.

EXAMPLE 9

Except that an epoxy resin was used in which the ligand to be introduced into the resin was changed to a dicarbonyl group expressed by the chemical formula 8 below, the constitutions were the same as in Example 1.

(chemical formula 8)

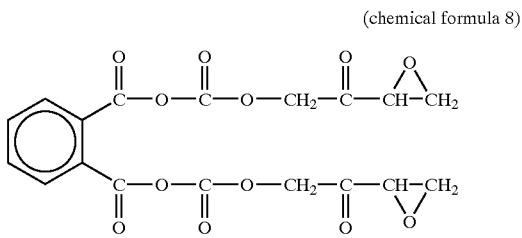

As a result, in comparison with the cases of Comparative Example 1 (a conventional conductive adhesive), Comparative Example 5 (a silane coupling agent was added), and Comparative Example 7 (an epoxy resin into which a phosphoric ester group was introduced), the amount of deflection at the time of NG rose, and the adhesive strength against the bending stress improved.

EXAMPLE 10

Except that the electrode was changed to a calcined Cu thick foil, the constitutions were the same as in Example 9.

As a result, in comparison with the cases of Comparative Example 2 (a conventional conductive adhesive), Comparative Example 6 (a silane coupling agent was added), and Comparative Example 8 (an epoxy resin into which a phosphoric ester group was introduced), the amount of deflection at the time of NG rose, and the adhesive strength against the bending stress improved.

EXAMPLE 11

Except that an epoxy resin was used in which the ligand to be introduced into the resin was changed to a dicarbonyl group expressed by the chemical formula 9 below, the constitutions were the same as in Example 1.

(chemical formula 9)

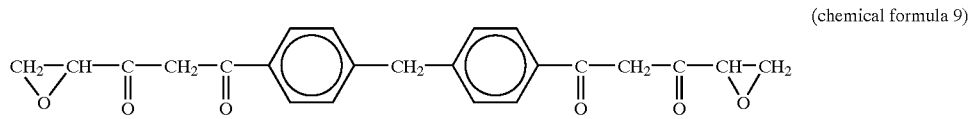

As a result, in comparison with the cases of Comparative Example 1 (a conventional conductive adhesive), Comparative Example 5 (a silane coupling agent was added), and Comparative Example 7 (an epoxy resin into which a phosphoric ester group was introduced), the amount of deflection at the time of NG rose, and the adhesive strength against the bending stress improved.

EXAMPLE 12

Except that the electrode was changed to a calcined Cu thick foil, the constitutions were the same as in Example 11.

As a result, in comparison with the cases of Comparative Example 2 (a conventional conductive adhesive), Comparative Example 6 (a silane coupling agent was added), and Comparative Example 8 (an epoxy resin into which a phosphoric ester group was introduced), the amount of deflection at the time of NG rose, and the adhesive strength against the bending stress improved.

EXAMPLE 13

Except that an epoxy resin was used in which the ligand to be introduced into the resin was changed to a dicarbonyl group expressed by the chemical formula 10 below (where n indicates a degree of polymerization of about 2 in average), the constitutions were the same as in Example 1.

(chemical formula 10)

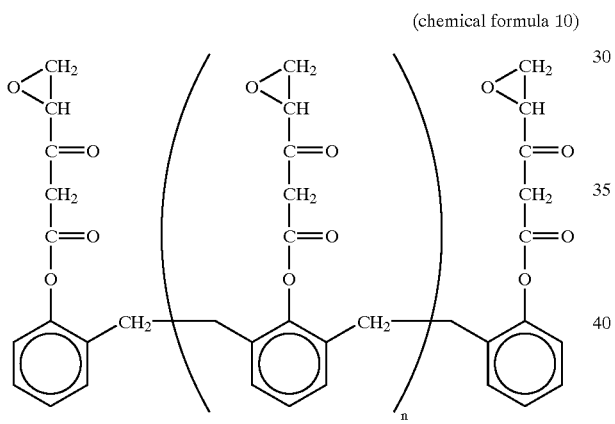

As a result, in comparison with the cases of Comparative Example 1 (a conventional conductive adhesive), Comparative Example 5 (a silane coupling agent was added), and Comparative Example 7 (an epoxy resin into which a phosphoric ester group was introduced), the amount of deflection at the time of NG rose, and the adhesive strength against the bending stress improved.

EXAMPLE 14

Except that the electrode was changed to a calcined Cu thick foil, the constitutions were the same as in Example 13.

As a result, in comparison with the cases of Comparative Example 2 (a conventional conductive adhesive), Comparative Example 6 (a silane coupling agent was added), and Comparative Example 8 (an epoxy resin into which a phosphoric ester group was introduced), the amount of deflection at the time of NG rose, and the adhesive strength against the bending stress improved.

COMPARATIVE EXAMPLE 1

Except that a conventional conductive adhesive of the following composition was used in place of the binder resin in Example 1, the experiment was performed in the same manner as in Example 1.

bisphenol F-type epoxy resin 90 wt %
hardener (diethylenetriamine) 5 wt %
solvent (butyl carbitol acetate) 5 wt %

COMPARATIVE EXAMPLE 2

Except that a calcined Cu thick foil was used in place of the Cu foil in Comparative Example 1, the experiment was performed in the same manner as in Comparative Example 1.

COMPARATIVE EXAMPLE 3

Except that a both-end hydrogen-dimethyl disilicone resin was used in place of the binder resin in Example 3, the experiment was performed in the same manner as in Example 1.

COMPARATIVE EXAMPLE 4

Except that a calcined Cu thick foil was used in place of the Cu foil in Comparative Example 3, the experiment was performed in the same manner as in Comparative Example 3.

COMPARATIVE EXAMPLE 5

Except that a silane coupling agent was used in place of the binder resin in Example 1, the experiment was performed in the same manner as in Example 1.

COMPARATIVE EXAMPLE 6

Except that a calcined Cu thick foil was used in place of the Cu foil in Comparative Example 5, the experiment was performed in the same manner as in Comparative Example 5.

COMPARATIVE EXAMPLE 7

Except that an epoxy resin in which a phosphoric ester group was introduced into its molecular skeleton was used in place of the binder resin in Example 1, the experiment was performed in the same manner as in Example 1.

COMPARATIVE EXAMPLE 8

Except that a calcined Cu thick foil was used in place of the Cu foil in Comparative Example 7, the experiment was performed in the same manner as in Comparative Example 7.

All the results of Examples 1 to 14 and Comparative Examples 1 to 8 above of the present invention are shown in Table 1 below.

TABLE 1-1

| | Conductive Adhesive | | | |
|---|---|---|---|---|
| | Binder Resin | | Rate of Content | |
| Experimental | Resin introduced with ligand | | (in total resin) | Conductive |
| No. | Skeleton | Ligand | (wt %) | particle |
| Example 1 | epoxy | dicarbonyl group | 15 | Ag |
| Example 2 | epoxy | dicarbonyl group | 15 | Ag |
| Example 3 | silicone | dicarbonyl group | 15 | Ag |
| Example 4 | silicone | dicarbonyl group | 15 | Ag |
| Example 5 | epoxy | aminocarbonyl group | 15 | Ag |
| Example 6 | epoxy | aminocarbonyl group | 15 | Ag |
| Example 7 | epoxy | dicarbonyl group | 15 | Ag |
| Example 8 | epoxy | dicarbonyl group | 15 | Ag |
| Example 9 | epoxy | dicarbonyl group | 15 | Ag |
| Example 10 | epoxy | dicarbonyl group | 15 | Ag |
| Example 11 | epoxy | dicarbonyl group | 65 | Ag |
| Example 12 | epoxy | dicarbonyl group | 65 | Ag |
| Example 13 | epoxy | dicarbonyl group | 65 | Ag |
| Example 14 | epoxy | dicarbonyl group | 65 | Ag |
| Compar. Example 1 | epoxy | none | 0 | Ag |
| Compar. Example 2 | epoxy | none | 0 | Ag |
| Compar. Example 3 | silicone | none | 0 | Ag |
| Compar. Example 4 | silicone | none | 0 | Ag |
| Compar. Example 5 | epoxy | none (silane coupling agent added) | 0 | Ag |
| Compar. Example 6 | epoxy | none (silane coupling agent added) | 0 | Ag |
| Compar. Example 7 | epoxy | a phosphoric ester group | 15 | Ag |
| Compar. Example 8 | epoxy | a phosphoric ester group | 15 | Ag |

TABLE 1-2

| | Substrate and Component | | | | Results of Bending Test | |
|---|---|---|---|---|---|---|
| | | Electrode Specification | | | Deflection at | Initial |
| Experimental No. | Base Material | Material | Porosity (vol%) | Roughness (μm) | the time of NG (mm) | Resistance (Ω) |
| Example 1 | glass epoxy | Cu foil | — | 0.1 | 7.5 | 0.15 |
| Example 2 | alumina | calcined Cu thick foil | 2.0 | — | 9.6 | 0.20 |
| Example 3 | glass epoxy | Cu foil | — | 0.1 | 8.9 | 0.20 |
| Example 4 | alumina | calcined Cu thick foil | 2.0 | — | 10.7 | 0.20 |
| Example 5 | glass epoxy | Cu foil | — | 0.1 | 7.3 | 0.15 |
| Example 6 | alumina | calcined Cu thick foil | 2.0 | — | 9.9 | 0.18 |
| Example 7 | glass epoxy | Cu foil | — | 0.1 | 7.4 | 0.16 |
| Example 8 | alumina | calcined Cu thick foil | 2.0 | — | 9.8 | 0.15 |
| Example 9 | glass epoxy | Cu foil | — | 0.1 | 7.6 | 0.12 |
| Example 10 | alumina | calcined Cu thick foil | 2.0 | — | 9.9 | 0.15 |
| Example 11 | glass epoxy | Cu foil | — | 0.1 | 7.7 | 0.22 |
| Example 12 | alumina | calcined Cu thick foil | 2.0 | — | 10.0 | 0.20 |
| Example 13 | glass epoxy | Cu foil | — | 0.1 | 7.8 | 0.21 |
| Example 14 | alumina | calcined Cu thick foil | 2.0 | — | 10.1 | 0.19 |
| Compar. Example 1 | glass epoxy | Cu foil | — | 0.1 | 2.4 | 0.20 |
| Compar. Example 2 | alumina | calcined Cu thick foil | 2.0 | — | 2.8 | 0.20 |
| Compar. Example 3 | glass epoxy | Cu foil | — | 0.1 | 0.7 | 0.20 |

TABLE 1-2-continued

| | Substrate and Component | | | | Results of Bending Test | |
|---|---|---|---|---|---|---|
| | | Electrode Specification | | | Deflection at | Initial |
| Experimental No. | Base Material | Material | Porosity (vol%) | Roughness (μm) | the time of NG (mm) | Resistance (Ω) |
| Compar. Example 4 | alumina | calcined Cu thick foil | 2.0 | — | 0.9 | 0.20 |
| Compar. Example 5 | glass epoxy | Cu foil | — | 0.1 | 3.2 | 0.10 |
| Compar. Example 6 | alumina | calcined Cu thick foil | 2.0 | — | 3.3 | 0.20 |
| Compar. Example 7 | glass epoxy | Cu foil | — | 0.1 | 3.8 | 0.20 |
| Compar. Example 8 | alumina | calcined Cu thick foil | 2.0 | — | 4.2 | 0.20 |

In the Examples of the present invention above, the binder resins used for the conductive adhesive were only an epoxy resin and a silicone resin, but other resins described in the Embodiments also are effective for use. Moreover, only a dicarbonyl group was shown as the ligand bonded to the side chain of the binder resin, but other ligands described in the Embodiments also may be used. Furthermore, only copper was used as the electrode metal, but other metals generally used for electrodes as described in the Embodiments also may be used.

According to the present invention, the problems with regard to the mounting of conductive adhesives, i.e. the adhesive strength and particularly the strength against the bending stress, can be solved easily. The present invention greatly contributes to the commercial application of the mounting technique using conductive adhesives.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A conductive adhesive comprising a binder resin and a metal filler as main components, wherein the binder resin contains a functional group in its molecular chain that forms a multidentate bonding with an electrode metal after the binder resin is adhered, wherein taking the conductive adhesive as 100 wt %, the binder resin is contained in an amount between 5 and 25 wt %, and the metal filler is contained in an amount between 75 and 95 wt %.

2. The conductive adhesive according to claim 1, wherein the multidentate bonding is formed in a number between 2 and 4 per molecule.

3. The conductive adhesive according to claim 1, wherein the resin containing a functional group in its molecular chain that forms a multidentate bonding is present in an amount between 10 and 100 wt % of the total resin.

4. The conductive adhesive according to claim 1, wherein at least two functional groups are present, which may be the same or different, selected from the group consisting of a carbonyl groups a carboxyl group, an amino group, an imino group, an iminoacetic acid group, an iminopropionic acid group, a hydroxyl group, a thiol group, a pyridinium group, an imido group, an azo group, a nitrilo group, an ammonium group and an imidazole group.

5. The conductive adhesive according to claim 1, wherein the metal filler is at least one particle selected from the group consisting of silver, silver-plated nickel and silver-plated copper.

6. The conductive adhesive according to claim 1, wherein the binder resin is at least one resin selected from a thermoplastic resin and a thermosetting resin.

7. The conductive adhesive according to claim 6, wherein the thermoplastic resin is at least one resin selected from the group consisting of a polyester resin, a silicone resin, a vinyl resin, a vinyl chloride resin, an acrylic resin, a polystyrene resin, an ionomer resin, a polymethylpentene resin, a polyimide resin, a polycarbonate resin, a fluororesin and a thermoplastic epoxy resin.

* * * * *

UNITED STATES PATENT AND TRADEMARK OFFICE
CERTIFICATE OF CORRECTION

PATENT NO. : 6,749,774 B2
DATED : June 15, 2004
INVENTOR(S) : Takezawa et al.

It is certified that error appears in the above-identified patent and that said Letters Patent is hereby corrected as shown below:

Column 14,
Line 32, "carbonyl groups a carboxyl" should read -- carbonyl group, a carboxyl --.

Signed and Sealed this

Eleventh Day of October, 2005

JON W. DUDAS
*Director of the United States Patent and Trademark Office*